US012579651B2

(12) United States Patent
Malyarenko et al.

(10) Patent No.: US 12,579,651 B2
(45) Date of Patent: Mar. 17, 2026

(54) IMPEDED DIFFUSION FRACTION FOR QUANTITATIVE IMAGING DIAGNOSTIC ASSAY

(71) Applicant: REGENTS OF THE UNIVERSITY OF MICHIGAN, Ann Arbor, MI (US)

(72) Inventors: Dariya I. Malyarenko, Ann Arbor, MI (US); Scott D. Swanson, Ann Arbor, MI (US); Thomas L. Chenevert, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 650 days.

(21) Appl. No.: 17/886,027

(22) Filed: Aug. 11, 2022

(65) Prior Publication Data

US 2023/0053434 A1 Feb. 23, 2023

Related U.S. Application Data

(60) Provisional application No. 63/260,185, filed on Aug. 11, 2021.

(51) Int. Cl.
$$
\begin{array}{lll}
\textit{G06T 7/00} & (2017.01) \\
\textit{A61B 5/00} & (2006.01) \\
\textit{G01R 33/563} & (2006.01)
\end{array}
$$

(52) U.S. Cl.
CPC .......... G06T 7/0016 (2013.01); A61B 5/4842 (2013.01); A61B 5/4848 (2013.01); G01R 33/56341 (2013.01); G06T 2207/10088
(2013.01); G06T 2207/30068 (2013.01); G06T 2207/30081 (2013.01); G06T 2207/30096 (2013.01)

(58) Field of Classification Search
None
See application file for complete search history.

(56) References Cited

U.S. PATENT DOCUMENTS

| | | | | |
|---|---|---|---|---|
| 2012/0280686 A1* | 11/2012 | White | .................... | G01R 33/48 |
| | | | | 324/309 |
| 2016/0139226 A1* | 5/2016 | Manikis | ............. | G01R 33/5608 |
| | | | | 703/2 |
| 2017/0124294 A1* | 5/2017 | Perez | ....................... | G06F 17/18 |
| 2018/0271373 A1* | 9/2018 | Kim | ......................... | A61B 5/00 |
| 2019/0150822 A1* | 5/2019 | Wang | .................. | A61B 5/4088 |
| 2021/0104045 A1* | 4/2021 | Blamire | ................ | G06T 7/0012 |

OTHER PUBLICATIONS

Garcia-Figueiras et al., "How clinical imaging can assess cancer biology," Insights Into Imaging, Springer Open Access, 2019, https://doi.org/10.1186/s13244-019-0703-0. (Year: 2019).*

(Continued)

*Primary Examiner* — Michelle M Koeth
(74) *Attorney, Agent, or Firm* — MARSHALL, GERSTEIN & BORUN LLP

(57) ABSTRACT

Methods and systems are provided for analyzing diffusion weighted images (DWI) using impeded diffusion fraction models for quantitative imaging diagnostic assay of cancer, such as glandular tissue cancers. The Impeded diffusion fraction models are tissue and cancer independent and generate a single score representative of multi-compartment diffusion fractions occurring within each voxel of a DWI image.

19 Claims, 8 Drawing Sheets

(56) References Cited

OTHER PUBLICATIONS

Panagiotaki et al., "Noninvasive Quantification of Solid Tumor Microstructure Using VERDICT MRI," Cancer Res Apr. 1, 2014; 74 (7): 1902-1912. https://doi.org/10.1158/0008-5472.CAN-13-2511. (Year: 2014).*

Hill et al., "Non-Invasive Prostate Cancer Characterization with Diffusion-Weighted MRI: Insight from In silico Studies of a Transgenic Mouse Model," Frontiers in Oncology, Dec. 1, 2017, vol. 7, Article 290, 10.3389/fonc.2017.00290. (Year: 2017).*

Auffenberg et al., A Roadmap for Improving the Management of Favorable Risk Prostate Cancer, J. Urol., 198(6):1220-1222 (2017).

Barkovich et al., A Systematic Review of the Existing Prostate Imaging Reporting and Data System Version 2 (PI-RADSv2) Literature and Subset Meta-Analysis of PI-RADSv2 Categories Stratified by Gleason Scores, American Journal of Roentgenology, 212 (4) : 847-854 (2019).

Bojorquez et al., What are normal relaxation times of tissues at 3 T?, Magn. Reson. Imag., 35:69-80 (2017).

Carlin et al., Probing structure of normal and malignant prostate tissue before and after radiation therapy with luminal water fraction and diffusion-weighted MRI, Journal of Magnetic Resonance Imaging, 50 (2) : 619-627 (2019).

Chatterjee et al., Diagnosis of Prostate Cancer with Noninvasive Estimation of Prostate Tissue Composition by Using Hybrid Multidimensional MR Imaging: A Feasibility Study, Radiol., 287(3):864-873 (2018).

Dyvorne et al., Intravoxel incoherent motion diffusion imaging of the liver: Optimal b-value subsampling and impact on parameter precision and reproducibility, European Journal of Radiology, 83 (12) : 2109-2113 (2014).

Gilani et al., A Model Describing Diffusion in Prostate Cancer, Magn. Reson. Med., 78(1):316-326 (2017).

Hectors et al., Advanced Diffusion-weighted Imaging Modeling for Prostate Cancer Characterization: Correlation with Quantitative Histopathologic Tumor Tissue Composition—A Hypothesis-generating Study, Radiology, 286 (3) : 918-928 (2018).

Holz et al., Temperature-dependent self-diffusion coefficients of water and six selected molecular liquids for calibration in accurate 1H NMRPFG measurements, Physical Chemistry Chemical Physics, 2 (20) : 4740-4742 (2000).

Hurrell et al., Optimized b-value selection for the discrimination of prostate cancer grades, including the cribriform pattern, using diffusion weighted imaging, Journal of Medical Imaging, 5 (1) : 011004(1-16) (2018).

Iima et al., Clinical Intravoxel Incoherent Motion and Diffusion MR Imaging: Past, Present, and Future, Radiology, 278 (1) : 13-32 (2016).

Inaba, Quantitative Measurements of Prostatic Blood Flow and Blood Volume by Positron Emission Tomography. J. Urol., 148:1457-1460 (1992).

Jensen et al., MRI quantification of non-Gaussian water diffusion by kurtosis analysis, NMR in Biomedicine, 23 (7) : 698-710 (2010).

Johnston et al., VERDICT MRI for Prostate Cancer: Intracellular Volume Fraction versus Apparent Diffusion Coefficient, Radiol., 291(2):391-397 (2019).

McHugh et al., Towards a 'resolution limit' for DW-MRI tumor microstructural models: A simulation study investigating the feasibility of distinguishing between microstructural changes, Magn. Reson. Med., 81(4):2288-2301 (2019).

Panagiotaki et al., Microstructural characterization of normal and malignant human prostate tissue with vascular, extracellular, and restricted diffusion for cytometry in tumours magnetic resonance imaging, Investigative Radiology, 50 (4) : 218-227 (2015).

Pierpaoli et al., Polyvinylpyrrolidone (PVP) Water Solutions as Isotropic Phantoms for Diffusion MRI Studies, International Society for Magnetic Resonance in Medicine, 17 (1) : 1414 page (2019).

Polnaszek et al., Self-Diffusion of Water at the Protein Surface: A Measurement, J. Am. Chem. Soc., 106:428-429 (1984).

Pullens et al., Technical Note: A safe, cheap, and easy-to-use isotropic diffusion MRI phantom for clinical and multicenter studies, Med. Phys., 44(3):1063-1070 (2017).

Purysko et al., PI-RADS Version 2: A Pictorial Update, RadioGraphics, 36(5):1354-1372 (2016).

Rashid et al., Novel use for polyvinylpyrrolidone as a macromolecular crowder for enhanced extracellular matrix deposition and cell proliferation, Tissue Engineering Part C: Methods, 20 (12) : 994-1002 (2014).

Rosenkrantz et al., Body diffusion kurtosis imaging: Basic principles, applications, and considerations for clinical practice, Journal of Magnetic Resonance Imaging, 42 (5) : 1190-1202 (2015).

Shankar et al., Temporary Health Impact of Prostate MRI and Transrectal Prostate Biopsy in Active Surveillance Prostate Cancer Patients, J. Urol., 148:1457-1460 (1992).

Stanisz et al., T1, T2 Relaxation and Magnetization Transfer in Tissue at 3T, Magn. Reson. Med., 54(3):507-12 (2005).

Swanson et al., Tunable diffusion kurtosis in lamellar vesicle suspensions toward development of quantitative phantom surrogate of tumor microenvironment, Proceedings of the International Society for Magnetic Resonance in Medicine, 1-3 (2019).

Trovato et al., Diffusion within the Cytoplasm: A Mesoscale Model of Interacting Macromolecules, Biophysical journal, 107 (11) : 2579-2591 (2014).

* cited by examiner

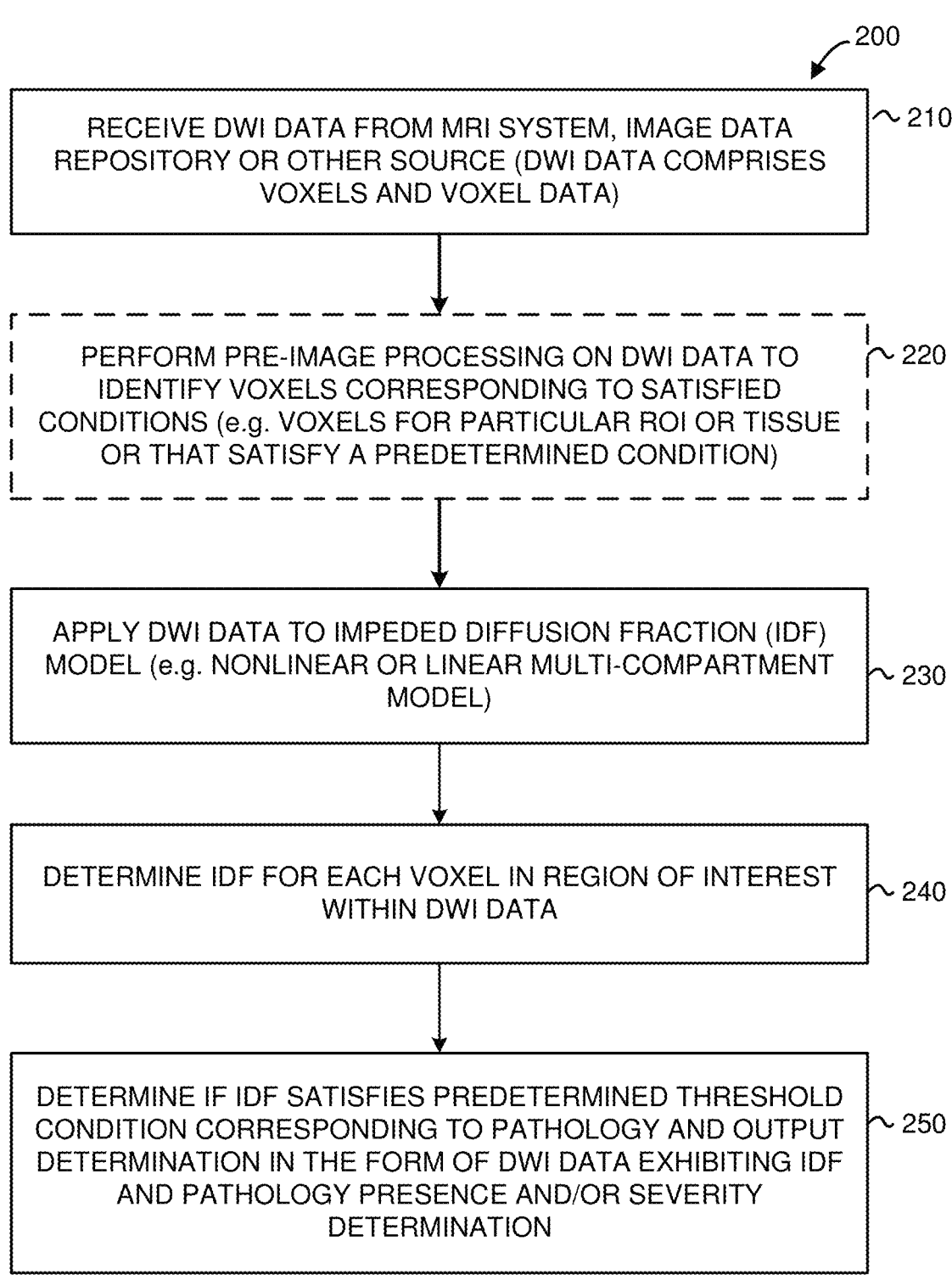

RECEIVE DWI DATA FROM MRI SYSTEM, IMAGE DATA REPOSITORY OR OTHER SOURCE (DWI DATA COMPRISES VOXELS AND VOXEL DATA) ～ 210

PERFORM PRE-IMAGE PROCESSING ON DWI DATA TO IDENTIFY VOXELS CORRESPONDING TO SATISFIED CONDITIONS (e.g. VOXELS FOR PARTICULAR ROI OR TISSUE OR THAT SATISFY A PREDETERMINED CONDITION) ～ 220

APPLY DWI DATA TO IMPEDED DIFFUSION FRACTION (IDF) MODEL (e.g. NONLINEAR OR LINEAR MULTI-COMPARTMENT MODEL) ～ 230

DETERMINE IDF FOR EACH VOXEL IN REGION OF INTEREST WITHIN DWI DATA ～ 240

DETERMINE IF IDF SATISFIES PREDETERMINED THRESHOLD CONDITION CORRESPONDING TO PATHOLOGY AND OUTPUT DETERMINATION IN THE FORM OF DWI DATA EXHIBITING IDF AND PATHOLOGY PRESENCE AND/OR SEVERITY DETERMINATION ～ 250

*FIG. 2*

IMPEDED DIFFUSION FRACTION FOR QUANTITATIVE IMAGING DIAGNOSTIC ASSAY

CROSS-REFERENCE TO RELATED APPLICATIONS

This application claims priority to U.S. Provisional Application No. 63/260,185, filed Aug. 11, 2021, which is incorporated herein by reference in its entirety.

STATEMENT OF GOVERNMENT INTEREST

This invention was made with government support under CA166104 awarded by the National Institutes of Health. The government has certain rights in the invention.

FIELD OF THE DISCLOSURE

The invention generally relates to diffusion weighted imaging for changes in tissue density with application to cancer imaging and, in particular, to assessing impeded diffusion fraction (IDF) from diffusion weighted images for accurate pathology risk scoring in tissue.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Diffusion weighted imaging (DWI) based on endogenous contrast sensitive to tissue microstructure is an appealing imaging modality for cancer staging, active surveillance, and longitudinal treatment response monitoring. Conventional techniques use relative DWI intensities without specific models for analysis. Some have recently proposed analyzing DWI using quantitative (q)DWI models to derive tissue diffusion metrics.

However, while there have been advances in DWI models and acquisition protocols, rollout of effective qDWI techniques in clinical setting has been slow. The majority of clinical MRI protocols continue to use DWI qualitatively, and as an indicator of impeded diffusion evident from sustained signal at high b-values (diffusion gradient strength). When a quantitation of DWI is desired, conventional techniques use a mono-exponential (ME) diffusion model to derive apparent diffusion coefficient (ADC) from the fit signal dependence on b-value for a series of DWI acquisitions. For example, such techniques, use ADC (moderately correlated to inverse Gleason Score, GS), to aid imaging differentiation of indolent from aggressive prostate cancer, adhering to current clinical Prostate Imaging Reporting and Data Systems (PIRADS) guidelines. Although prostate cancer remains a high occurrence disease affecting close to 192,000 men per year in the United States alone and demanding extensive management resources, only 10-15% of PCa patient population tend to develop aggressive malignancy requiring radical treatment. For the majority of patients, active surveillance of low-grade prostate cancer using noninvasive prostate MRI improves patient quality-of-life over a prostate biopsy.

Due to inherently multi-exponential diffusion in complex tumor micro-environment, in practice, ADC values depend on technical acquisition features (e.g., b-value range and signal-to-noise ratio (SNR)), which limits the clinical robustness of quantitative differentiation between indolent and aggressive prostate cancers across varying clinical platforms and scan protocols. Furthermore, due to low SNR, current PIRADS recommend that high-b value DWI is used only qualitatively, disjoint from ADC. All these limitations contribute to a substantial false positive rate (e.g., upwards of 70%) for low-grade prostate cancer stratification by PIRADS. Several groups actively pursue investigation of alternative diffusion-derived metrics based on multi-compartment biophysical prostate cancer tumor models probed over a wide b-range. However, these models introduced to quantify multi-exponential DWI commonly rely on acquisition and organ-dependent assumptions about signal origin (compartment characteristics), have to be constrained to prevent non-physical parameters ranges (e.g., for perfusion and kurtosis component), and require specialized acquisition protocols, not routinely implemented in clinical imaging settings.

There is a need for unified models of DWI assessment and cancer type identification across different tissue types and across different b-value ranges for practical clinical implementation.

SUMMARY OF THE INVENTION

The present application describes techniques for quantitation of impeded diffusion fraction (IDF) for clinical diffusion weighted imaging (DWI) to improve diagnostic assay accuracy for cancer staging in tissue (e.g., in glandular tissue such as prostate, breast, pancreas). The techniques perform a deconvolution of IDF contribution from water coordinated by macromolecules to DWI voxel signals using a model based on scaling diffusion rates. The model, for example, can include order of magnitude different diffusion rates corresponding to vascular, ductal lumen, and cellular tissue compartments. The result are techniques that can be deployed to develop quantitative imaging essays (with objective thresholds) for multiple organ cancers using common acquisition protocol parameters across different clinical scanners, and across different tissue and cancer types.

In some examples, the models are calibrated using a quantitative kurtosis diffusion phantom or other calibration techniques. In an example, the techniques herein were implemented for a series of prostate cancer (PCa) cases, with high and low grade lesions annotated from whole-mount histopathology. The techniques reduced false positive rates for PCa staging compared to conventional techniques such as ADC used by current standard-of-care (SOC) PIRADS scoring and conventional SOC DWI techniques.

In an example, a computer-implemented method of analyzing diffusion weighted images, the computer-implemented method comprises: receiving, at one or more processors, diffusion weighted image (DWI) data corresponding to a sample and identifying within the DWI data a region of interest comprising one or more voxels, the region of interest spanning at least partially a tissue region within the sample; applying, using the one or more processors, the DWI data corresponding to the region of interest to an impeded diffusion fraction model and, from applying the impeded diffusion fraction model, determining an impeded diffusion fraction for each of the one or more voxels in the region of interest, the impeded diffusion fraction model being a multi-compartment model of water coordination by macromolecules based on fixed, order of magnitude scaling rates for free diffusion, vascular diffusion, and coordinated diffusion; and from the impeded diffusion fraction of the one or more voxels, identifying the presence and/or severity of a pathology in the sample.

In an example, the impeded diffusion fraction model comprises a cellular compartment model, a free water compartment model, vascular compartment model.

In an example, the impeded diffusion fraction model comprises an expression for nonlinear impeded diffusion fraction (IDF):

$$\frac{S_b}{S_0} \approx F_f E_f + (1 - F_p - F_f) E_c; E_f = \exp(-bD_f); E_c \approx \exp(-bF_{fc}D_f);$$

$$IDF = 1 - F_p - F_f - F_{fc}$$

where $S_b$ is the DWI signal intensity as a function of b-value, $S_0$ is signal intensity at b=0, b are three or more b-values between 0.1 and 2 ms/µm² (one or more>1 ms/µm²) $D_f$ is free diffusion rate, $F_p$ is a pseudo diffusion fraction corresponding to a vascular compartment, $F_f$ is a free water diffusion fraction, and $F_{fc}$ is an uncoordinated water diffusion fraction in a cellular compartment.

In an example, the impeded diffusion fraction model comprises an expression for a linear impeded diffusion fraction (IDFL):

$$\log\left(\frac{S_b}{S_0}\right) = C_1 + C_2 \cdot b; F_{fc} = -C_2/D_f;$$

$$F_c = \exp(C_1); IDF_L = \exp(C_1) + C_2/D_f$$

where $S_b$ is the DWI signal intensity as a function of b-value, $S_0$ is signal intensity at b=0, C1 is a linear fit intercept, C2 is a linear fit slope, b are two or more b-values between 0.6 and 2 ms/µm² (one or more>1 ms/µm²) linear fit intercept, $D_f$ is free diffusion rate, and Fc is cellular fraction, for each of the one of more voxels.

In an example, the impeded diffusion fraction model comprises a nonlinear fit impeded diffusion fraction. In an example, the nonlinear fit impeded diffusion fraction comprises fit constraints.

In an example, the impeded diffusion fraction model comprises a linear fit impeded diffusion fraction. In an example, the linear fit impeded diffusion fraction comprises fit constraints.

In an example, the DWI data comprises image data of the sample and comprising a plurality of voxels, the method further comprises: prior to applying the DWI data to impeded diffusion fraction model, identifying from the plurality of voxels, voxels satisfying a threshold voxel signal threshold condition and applying, as the DWI data, those voxels satisfying the threshold voxel signal threshold condition.

In an example, the DWI data comprises image data of the sample and comprising a plurality of voxels, the method further comprises: prior to applying the DWI data to impeded diffusion fraction model, identifying from the plurality of voxels, voxels corresponding to a boundary region between normal tissue and lesion indicating tissue, and excluding, from the DWI data, those voxels corresponding to the region boundary.

In an example, the DWI data comprises a plurality of voxels and wherein identifying the presence of a pathology in the sample comprises: determining the impeded diffusion fraction for each of a plurality of voxels, determining a statistical summary metric of impeded diffusion fraction from the plurality of impeded diffusion fractions, and identifying the presence of the pathology from the summary metric for impeded diffusion fraction. In an example, the statistical summary metric is an average, a median, a standard deviation, or percentile. In an example, the statistical summary metric for plurality of voxels within region of interest is any mathematical histograms characteristic (moment), or percentile In an example, identifying the presence of a pathology in the sample comprises: determining if the impeded diffusion fraction is above a threshold value of a statistical summary metric, the threshold value corresponding to the presence of the pathogen.

In an example, identifying the presence of a pathology in the sample comprises: determining if the impeded diffusion fraction is above a threshold value, the threshold value corresponding to the presence of the pathogen.

In an example, the pathogen is cancer.

In an example, the pathogen is cancer severity.

In an example, the cancer is prostate cancer, breast cancer, or pancreatic cancer.

In an example, a threshold value is determined from retrospective DWI analysis and adjusted for acquisition protocol bias in T1 and T2 weighting and b-range.

In an example, the pathology is cancer and the sample is taken from disease tissue, the method further comprises, after performing a treatment on the subject: receiving, at one or more processors, subsequent DWI data corresponding to a subsequent sample taken from the disease tissue, and identifying within the subsequent DWI data one or more voxels corresponding to the region of interest; applying, using the one or more processors, the subsequent DWI data to the impeded diffusion fraction model and determining the presence of a change in the impeded diffusion fraction from the impeded diffusion fraction determined from the DWI data; and from the presence of the change in the impeded diffusion fraction, determining an efficacy of the treatment on the subject.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 2 is process diagram of a method for assessing impeded diffusion fraction in diffusion weighted image data as may be performed by the system of FIG. 1.

FIGS. 4A and 4B show IDF model-based single-voxel fit for acquired log-DWI data (asterisks) as a function of b-value (fit fractions summarized in Table 1). Dashed vertical lines mark b-value subset tested for the SOC protocol.

FIGS. 6B and 6C illustrate linear dependence for phantom IDF titration and $IDF_L$ bias trend, respectively.

DETAILED DESCRIPTION

The present application describes techniques for quantitation of impeded diffusion fraction (IDF) for clinical diffusion weighted imaging (DWI) to improve diagnostic assay accuracy for cancer staging in tissue (e.g., in glandular tissue rich in secretory ducts, such as prostate, breast, pancreas). The techniques perform a deconvolution of IDF contribution from water coordinated by macromolecules to DWI voxel signals using a model based on scaling diffusion rates. The model, for example, can include an order of magnitude different diffusion rates corresponding to vascular, ductal lumen, and sub-cellular tissue compartments. The result are techniques that can be deployed to develop quantitative imaging essays (with objective thresholds) for multiple organ cancers using common acquisition protocol across different clinical scanners, with DWI settings, and across different tissue and cancer types.

Figure 1:
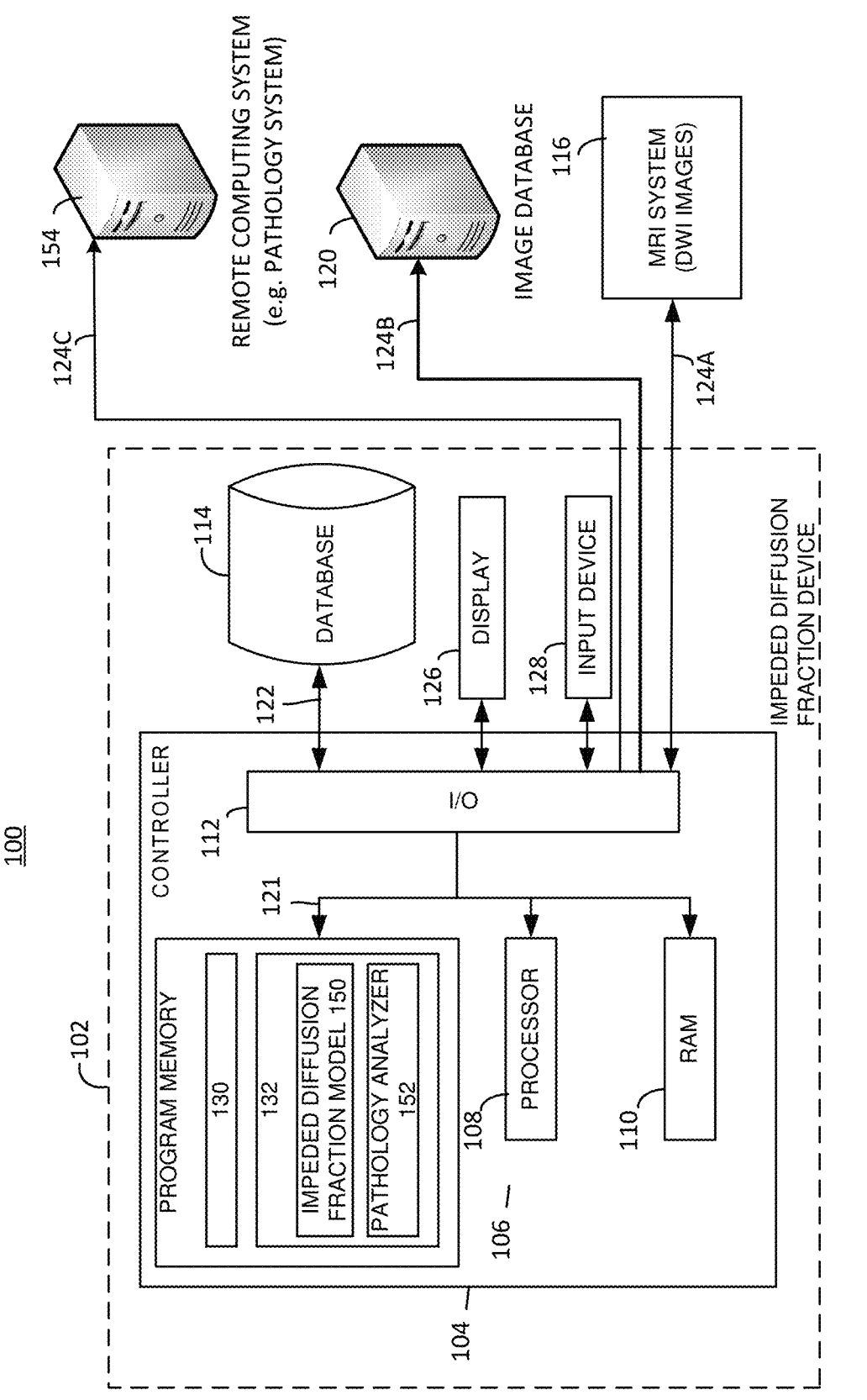
FIG. 1 is a block diagram of a schematic diagram of an example of diffusion weighted image analysis system.

FIG. 1 shows an example block diagram 100 illustrating the various components used in implementing an example embodiment of the present techniques. A signal-processing device 102 (or "signal processor" or "diagnostic device") is configured to collect image data, in particular diffusion weighted image (DWI) data from an imaging system (or imaging machine) 116, which may be an magnetic resonance imaging (MRI) system. That is, the signal-processing device 102 may be an impeded diffusion fraction device. In some examples, the signal-processing device 102 collects DWI image from an MRI image database 120 or other network accessible image storage for retrospective analysis, as shown.

The signal-processing device 102 may have a controller 104 operatively connected to a database 114 via a link 122 connected to an input/output (I/O) circuit 112. It should be noted that, while not shown, additional databases may be linked to the controller 104 in a known manner. The controller 104 includes a program memory 106, one or more processors 108 (may be called microcontrollers or a microprocessors), a random-access memory (RAM) 110, and the input/output (I/O) circuit 112, all of which are interconnected via an address/data bus 721. It should be appreciated that although only one processor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. Links 124A, 124B, and 124C, which may include one or more wired and/or wireless (Bluetooth, WLAN, etc.) connections, may operatively connect the controller 104 to the imaging device 116, the image database 120, and a remote computer system 154 through the I/O circuit 112, respectively. In other examples, the imaging device 116 may be part of the signal-processing device 102.

The program memory 106 and/or the RAM 110 may store various applications (i.e., machine readable instructions) for execution by the processor 108. For example, an operating system 130 may generally control the operation of the signal-processing device 102 and provide a user interface to the signal-processing device 102 to implement data processing operations. The program memory 106 and/or the RAM 110 may also store a variety of subroutines 132 for accessing specific functions of the signal-processing device 102. By way of example, and without limitation, the subroutines 132 may include, among other things impeded diffusion fraction (IDF) model module 150 for receiving DWI image data from the MRI system 116 or image database 120, optionally for pre-processing that DWI video data, and for determining IDF for voxels of interest in that DWI image data. The subroutines 132 may further include a pathology analyzer module 152 that receives the IDF data from the module 150 and identifies a pathology in a sample, such as whether the same contains cancer tissue. The pathology analyzer module 152 may include subroutines for assessing the efficacy of a treatment by looking at changes in the measured IDF of the module 150 over time.

The subroutines 132 may also include other subroutines, for example, implementing software keyboard functionality, interfacing with other hardware in the signal processing device 102, etc. The program memory 106 and/or the RAM 110 may further store data related to the configuration and/or operation of the signal-processing device 102, and/or related to the operation of the one or more subroutines 132. For example, the data may be data gathered by the imaging device 116, data determined and/or calculated by the processor 108, etc. In addition to the controller 104, the signal-processing device 102 may include other hardware resources. The signal-processing device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input.

It may be advantageous for the signal-processing device 102 to communicate with a medical treatment device, medical data records storage device, or network (not shown) through any of a number of known networking devices and techniques (e.g., through a commuter network such as a hospital or clinic intranet, the Internet, etc.). For example, the signal-processing device may be connected to a pathologist system 154, a medical records database, hospital management processing system, healthcare professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

The system 100 may be implemented as computer-readable instructions stored on a single dedicated machine, for example, one with one or more computer processing units. In some examples, the dedicated machine performs only the functions described in the processes of FIG. 2, and any other functions needed to perform those processes. The dedicated machine may be a standalone machine or embedded within another computing machine, such as system 100. In other examples, the functions described in FIG. 2 are integrated within an existing computing machine.

In some examples, one or more of the functions of the system 100 may be performed remotely, including, for example, on a server connected to a medical imaging device (such as system 100), through a wired or wireless interface and network. Such distributed processing may include having all or a portion of the processing of system 100 performed on a remote server. In some embodiments, the techniques herein may be implemented as software-as-a-service (SaaS) with the computer-readable instructions to perform the method steps being stored on one or more the computer processing devices and communicating with one or more user devices.

In example implementations, the techniques herein incorporate an impeded diffusion fraction (IDF) model (e.g., the IDF model 150) that is built as a multi-compartment model. The IDF model is constructed to include diffusion characteristics of different diffusion phenomena (e.g., sub-cellular, free, and perfused diffusion traits), combined into a singular model framework. The result is a single IDF metric that may be used to assess tumor density from diffusion MR images on a voxel-by-voxel basis and thus may be used as a single metric pathology biomarker, such as a cancer biomarker for diffusion images.

FIG. 2 illustrates an example process 200 for analyzing DWI data as may be performed by the impeded diffusion fraction device 102 of FIG. 1. At a block 210, DWI data is received (e.g., from the MRI system 116), that data including one or more voxels and voxel data, such as b values and other metadata associated with the capture diffusion MRI images. Optionally, a block 220 (e.g., as may implemented by the IDF model 150) performs pre-image processing on the DWI data, for example, to identify voxels that correspond to a desired region of interest or tissue lesion type, using DWI (e.g., high-b and b=0) and auxiliary anatomic images by manual or computer-aided segmentation. For example, to identify a region of interest the block 220 may identify voxels that corresponding to normal tissue within the a DWI data and, more specifically, in some examples, to voxels corresponding to the target lesion tissue and not voxels corresponding to edge regions between lesions of different types (e.g. atrophy versus cancer) in the DWI data and image data. Segmentation may be performed through manual processes from user input, for example, using a GUI. However, segmentation may be automated using image processing to identify features associated with target lesion tissue, including through the use of trained segmentation models. In some examples, the block 220 identifies voxels having a threshold signal value to allow for analysis of only voxels of sufficient intensity versus instrumental noise. In some examples, the block 220 identifies voxels that are registered to high-resolution anatomical T1-weighted and/or T2-weighted images for precise lesion delineation. Thus, in some examples, the block 220 identifies voxels corresponding to a boundary region between normal tissue and lesion/target tissue and excludes the voxels corresponding to the region boundary from IDF analysis.

Figure 3:
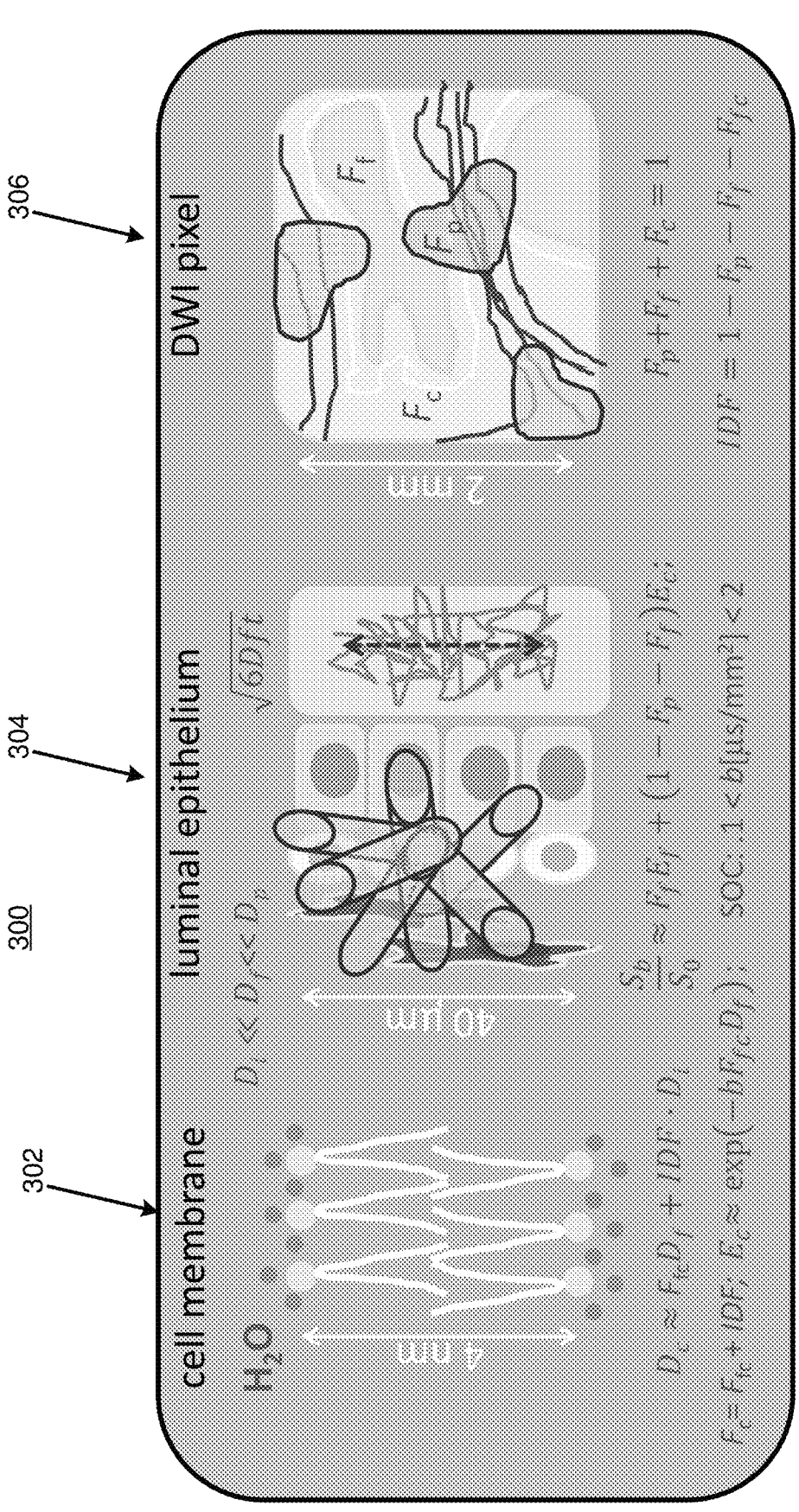
FIG. 3 illustrates construction of an example IDF model. A left side of the IDF model illustrates a sub-cellular compartment modeling of nanoscale water coordination, IDF, near a cell membrane (or macromolecules) effecting both intra- and extra-cellular water diffusion, in combination with an uncoordinated solvent water fraction, $F_{fc}$. A middle section of the IDF model illustrates micro-scale tissue compartments combining sub-cellular diffusion signal, $F_c E_c$, with free diffusion signal, $F_f E_f$, in luminal space (blue) or large-cell space (e.g., stromal fibroblast shown in purple), and pseudo-diffusion signal (vascular perfusion, $F_pE_p$) in randomly oriented capillaries (shown in red). A right side of the IDF model illustrates a millimeter scale partial volume contributions to a typically sized, clinical DWI pixel (2×2 $mm^2$) from sub-cellular, bulk free, and perfused tissue regions. A resulting formulation of the IDF model is shown with built-in constraints on diffusion rates ($D_i$: collective coordinated water; $D_f$: free water, $D_p$: vascular pseudo-diffusion) in tissue compartments over typical clinical DWI b-value range.

With one or more voxels of the DWI image data identified, a block 230 (e.g., as may implemented by the IDF model 150) then applies the voxels to an impeded diffusion fraction (IDF) model, such as that described in various examples herein, including FIG. 3. At a block 240 (e.g., as may implemented by the IDF model 150), the model determines, for each voxel provided to it, an IDF value. In various implementations, the IDF is a single value assessing the DWI image voxel. In examples where multiple voxels are being assessed, the block 240 may not only determine an IDF for each voxel, but further determine an IDF for grouping of voxels, such as a mean IDF for an entire region of interest or an IDF (or mean IDF) for a first tissue lesion type in an DWI image and another IDF (or mean IDF) for a second tissue lesion type in the DWI data.

At a block 250 (e.g., as may implemented by the IDF model 150), the IDF value(s) from the block 240 are processed to determine if a threshold value is satisfied, that threshold value corresponding to an indication of a pathology, such as the presence of prostate cancer. In some examples, the block 250 assess the IDF value(s) against multiple ranges of values, for example, each range corresponding to a different Gleason score for prostate cancer staging. More generally, however, the block 250 may identify one or more threshold values indicating the presence of cancer, cancer type, and/or cancer severity for any number of different tissue types, such as glandular tissues. The block 250 may further output the pathology determination, for example, in the form of a DWI image with an IDF indication overlay or with lesion identification overlay, to indicate the location of the cancer stage within the region of interest.

In some examples, the process 200 may be implemented for numerous DWI data for determining changes over time. For example, subsequent DWI data corresponding to a subsequent sample taken from a disease tissue may be provided, where one or more voxels corresponding to the region of interest are identified within the subsequent DWI data. That subsequent DWI data may be provided to the IDF model at block 230 and, for each region of interest, the blocks 240 and 250 can determine the presence of a change in the impeded diffusion fraction from the impeded diffusion fraction determined from the DWI data. By having that subsequent DWI data result from known treatments to a subject, the presence of changes in the impeded diffusion fraction are then used (block not shown) to determine an efficacy of the treatment, whether the subject is responding positively or negatively to the treatment.

FIG. 3 illustrates an example IDF model 300 with built-in constraints on diffusion rates for an example clinical DWI protocol, as an example implementation of the IDF model 150. In some implementations, the IDF model includes a nano-scale (nanometers) subcellular diffusion compartment, a free water diffusion compartment, and a vascular pseudo-diffusion compartment. Three, corresponding compartment model diffusion scales are shown, 302, 304, and 306. The compartment model 302 illustrates nanoscale water coordination near or at a cell membrane (or macromolecules) effecting both intra- and extra-cellular diffusion. The compartment model 304 illustrates micro-scale (microns) free diffusion in luminal space (blue) or large-cell space (e.g., stromal fibroblast, in purple) and pseudo-diffusion in randomly oriented capillary (red). The millimeter scale model 306 illustrates partial volume contributions of cellular, bulk free, and perfused tissue for image intensity in a typical clinical DWI pixel.

An example description of a nano-scale diffusion compartment, e.g., compartment model 302, is as follows. Diffusion rate in solutions over narrow temperature range can be described by Arrhenius formalism, $D = A \cdot \exp(-E_0/RT)$, where A is molecule collision frequency factor and $E_a$ is thermal activation energy, physically related to molecular concentration and hydrogen bonding strength, respectively. In general, both parameters tend to increase with macromolecule solute concentration with respect to values for pure water. For a fixed temperature typical of thermally regulated body imaging, this relation can be generally expressed as $D = F \cdot D_w$ to factor out water diffusion components from those dependent on solute fractions ($F \approx A/A_w \cdot \exp(-(E_a - E_w)/RT)$). FIG. 3 illustrates an example nano-scale compartment as a cell membrane compartment model 302, modeling diffusion effects across a cell membrane. In the illustrated example, the IDF model 300 is configured with the assumption that there are two water pools present both in intra-cellular space and extra-cellular space with apparent diffusion rate, $D_c \approx Ffc \cdot D_f + IDF \cdot D_i$, for subcellular water fraction $F_c = F_{fc} + IDF$. In the cell membrane model 302, $D_f$ is the free water diffusion rate (dependent on temperature only) (e.g., 3 $\mu s^2/ms$ at body temperature of 37° C.) of uncoordinated water fraction, $F_{fc}$, and $D_i$ is an average collective diffusion rate of the IDF water coordinated around macromolecules and cell membranes (both inner and outer layers, FIG. 3). The $D_i$ rate is governed by the water-macromolecule interactions and is assumed to be much slower than water free diffusion ($^-0.03~\mu m^2/ms \ll D_f$) as observed by previous NMR and DLS studies.

For the IDF model 300, the two water pools weighted by their corresponding fractions contribute to DWI signal from subcellular (e.g. epithelium membranes) compartment as, $F_c E_c$; $E_c = \exp(-bD_c)$, where the b-value represent the strength of applied diffusion gradients by the MRI machine. For typical clinical DWI scanning with b<2 $ms/\mu m^2$, and with $D_i \ll D_f$, the following approximation is valid for the sub-cellular compartment model 302: $E_c \approx \exp(-bF_{fc}D_f)$.

The next compartment model 304, in the illustrated example, corresponds to micro-scale tissue effects on diffusion, such as that contributed by the luminal epithelium, ductal lumen, and perfused randomly oriented capillaries. As such, in addition to the DWI signal from sub-cellular component model 302, $F_c E_c$, the illustrated IDF model 300 includes contributions from bulk free diffusion fraction, $F_f$, e.g., in luminal ducts, $F_f E_f$, and pseudo diffusion, $F_p$, in randomly oriented capillaries, $F_p E_p$. With the inclusion of the corresponding constraints for the compartment diffusion rates, $D_i \ll D_f \ll D_p$, the result is a an expression $$\frac{S_b}{S_0} \approx F_f E_f + (1 - F_p - F_f) E_c;$$

$E_f = \exp(-bD_f)$ for the micro-scale compartment model of DWI signal, $S_b$, dependence on b-value 304.

The compartment fractions 306 are related as $F_p + F_f + F_c = 1$. In an example, for the compartment model 304, the pseudo-diffusion rate is determined by $^-5~\mu m$-capillary pressure gradient ($D_p > 30~\mu m^2/ms \gg D_f$) exceeding $D_f$, as measured, for example, by PET perfusion studies. Hence, the pseudo-diffusion in the compartment model 304 has a contribution to the DWI signal that becomes negligible for b>0.1 $ms/\mu m^2$.

Thus, for a typical sized clinical DWI voxel, i.e., sized to $^-10 \cdot mm^3$ clinical DWI voxel scale, and over a b range for typical standard of care (SOC) acquired b-values (between 0.1 and 2 $ms/\mu m^2$), with all contributing compartments at equilibrium in living tissue, and with diffusion rates fixed to fundamental values for $D_f$, $D_p$ and $D_i$, the IDF model 300 is simplified to fit three partial volume fraction from DWI signal, $S_b$, measured as a function of b-value:

$$\frac{S_b}{S_0} \approx F_f E_f + (1 - F_p - F_f)E_c; \qquad \text{Eq. 1a}$$

$$E_f = \exp(-bD_f); E_c \approx \exp(-bF_{fc}D_f);$$

$$IDF = 1 - F_p - F_f - F_{fc}. \qquad \text{Eq. 1b}$$

That is, in the illustrated example of FIG. 3, the IDF model 300 provides an IDF score that is a three-parameter function ($F_p$, $F_f$, and $F_{fc}$) as follows: IDF=1$-F_p-F_f-F_{fc}$. Thus, for the SOC DWI acquisition of 4 b-values, the IDF model 300 determines an IDF value by non-linear fit of the three-parameter model in Eq.1 (1a and 1b). Inclusion of one b-value between 1 and 2 ms/$\mu m^2$ improves IDF deconvolution by separating $F_f$ contribution. Further, it is worth noting that the derived fractions will generally depend on acquisition TR (MRI repetition time) and TE (MRI time to echo) as:

$$F = \frac{S_{0F}(1 - E1_F)E2_F}{\sum_F^{f,p,c} S_{0F}(1 - E1_F)E2_F}; E1 = \exp\left(-\frac{TR}{T1}\right); E2 = \exp\left(-\frac{TE}{T2}\right) \qquad \text{Eq. 2}$$

where $S_{0F}$ is full (unbiased) proton density MRI signal for the corresponding compartment fraction $F=F_f$, $F_p$, $F_c$. Thus, in some examples, the IDF model 300 includes both expressions Eq. 1 and Eq. 2. The acquisition-induced absolute bias in compartment fractions can be evaluated using tissue-compartment specific magnetization relaxation times T1 and T2, and applied acquisition parameters, TR and TE. This shows that consistent measurements (fixed bias) across acquisition protocols may be insured by using standardized TE and TR values. Acquisition protocol consistency and bias estimates would facilitate establishing robust diagnostic essay thresholds.

Alternatively, to generalize diagnostic essay thresholds, e.g., for retrospective analysis between two acquisition protocols with different TR and TE, the IDF model could be adjusted for the difference between corresponding IDF biases (e.g., derived from Eq. 2 and substituted in Eq. 1). For example, the typical compartment T1 and T2 values should be included along with the protocol-specific TR and TE into forward simulation of Eq.2, and the resulting bias subtracted from fractions fit by Eq.1.

In another example, the IDF model may be implemented in a simplified format for example where b>1 ms/$\mu m^2$, where bulk free water contribution is negligible independent of organ, allowing linear IDF fit with just three acquired b-values. For enhanced contrast-to-noise of dense-tumor IDF ($D_c$<1.5 $\mu m^2$/ms, $F_{fc}$<0.5), the IDF model predicts optimal acquisition b-range (two b-values) between 1<b<2 ms/$\mu m^2$ that minimizes free and capillary water contribution. For these conditions, IDF model (Eq.1) can be "linearized" to derive a linear $IDF_L$ as:

$$\log\left(\frac{S_b}{S_0}\right) = C_1 + C_2 \cdot b; F_{fc} = -C_2/D_f; \qquad \text{Eq. 3}$$

$$F_c = \exp(C_1); IDF_L = \exp(C_1) + C_2/D_f.$$

The fit bias for the $IDF_L$ derived from this model mainly depends on the $1^{st}$ b>0 value used and can be estimated by comparison with the non-linear fit IDF.

Figure 4B:
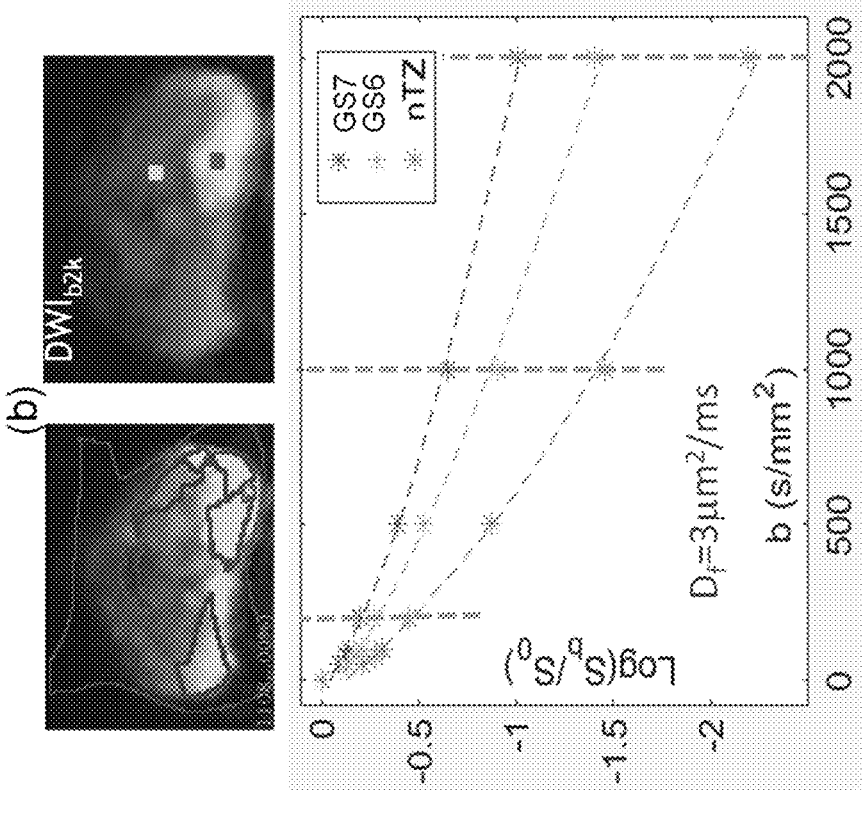
FIG. 4B illustrates a summary of prostate cancer (PCa) analysis. The top images show an example of PCa lesion annotations from whole-mount histopathology registered to b=0 DWI and traced on DWI (b=2 ms/μm²). Voxel samples for Gleason (GS) 6 and 7 and normal transition zone (nTZ), defined away from lesion boundaries, are color-coded for the IDF model fit data in the bottom plot legend. Dashed curves in the bottom plots of both
Figure 4A:
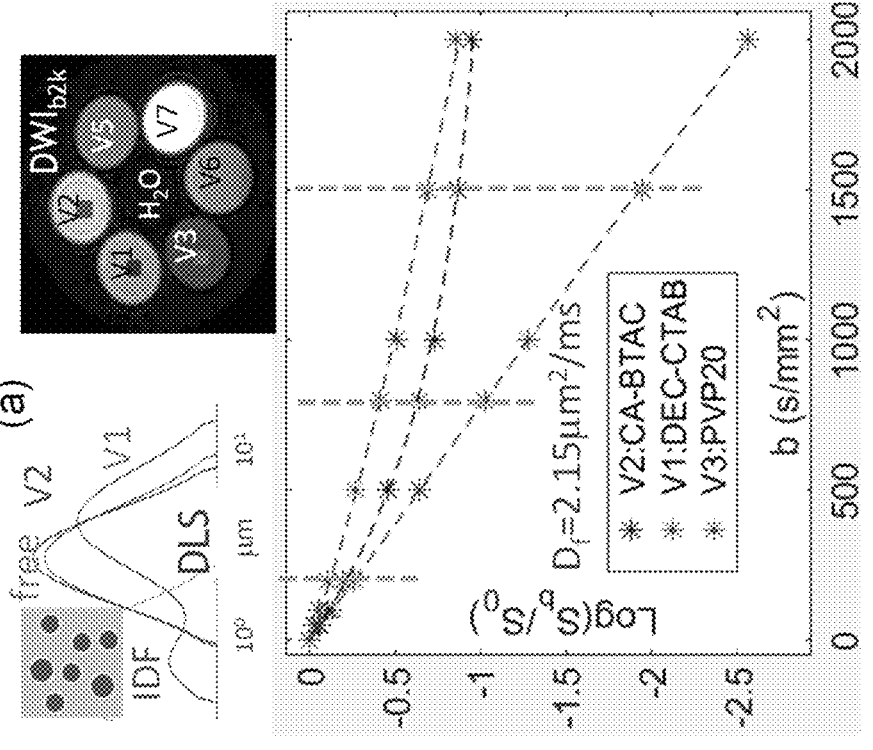
FIG. 4A illustrates a summary of DWI analysis of a phantom sample, showing in the top left labeled (a) dynamic light scattering (DLS) measurements for regions V1 and V2 of the phantom samples with inserts showing the schematic of their vesicular suspension comprised of free water compartments (light blue) and impeded (dark blue) water compartments. Shown are phantom DWI (b=2 ms/μm²) with material vial labels and color-coded voxel locations corresponding to IDF model fit data in the bottom plot legend. The chemical sample abbreviations in the legend denote CA: cetearyl alcohol, DEC: decyl alcohol, CTAB: cetyltrimethylammonium bromide, BTAC: behentriammonium chloride).

To assess the benefits of the techniques herein, we compared example implementations of the IDF model versus ADC and diffusion kurtosis (DK) parameters using previously described quantitative diffusion phantom material DWI (FIG. 4A-4B).

As shown in FIG. 4A, in the illustrated example, the diffusion phantom included materials with lamella vesicle suspension in bulk free water (e.g., V1, V2), which exhibited multi-exponential diffusion, and polyvinyl-pyrrolidone (PVP) solutions (V3, V5) with mono-exponential DWI. The impeded fraction in vesicular suspension was controlled by micro-scale vesicle size (V1:2.8 m, V2:1.6 m), measured by dynamic light scattering (DLS), while PVP concentration (V3:20%, V5:40%) determined nano-scale water coordination without bulk free water compartment. V1 and V2 provided model system with bulk, $F_f$, and vesicular, $F_{fc}$, from nanoscale lamella water compartments proportional to vesicle sizes V1:V2$^-$1.8. V3 and V5 provided single nanoscale hydration-coordination compartment (<10 nm, $F_f$=0), diffusion-rate scaling with solute concentration ($D_c$ (V3)/$D_c$(V5)=1.3/0.6$^-$2). Additional cetearyl alcohol (CA) cetyltrimethylammonium bromide (CTAB) vesicle samples (V7-family) with molar ratios from 3:1 to 6:1 (0.7 to 1.7 um sizes) and 0.5% to 2.5% (3:1) were used for IDF calibration and linear model (Eq. 3) fit bias analysis with respect to nonlinear fit (Eq. 1).

The phantom DWI images were acquired using b=0,0.05, 0.1,0.2,0.5,0.8,1,1.5,2,2.5.3 ms/$\mu m^2$, echo-time (TE)=105 ms, repetition-time (TR)=10 s, voxel-size (VS)=1.7×1.7×5 mm$^3$ Phantom $D_f$=2.15 $\mu m^2$/ms was measured at room temperature for V4 (0%-PVP) with $b_{max}$=1.5 ms/$\mu m^2$. The 8 and 4 b-value subsets of acquired 12 b-values over clinically relevant range 0.1<b<2 ms/$\mu m^2$ were used to compare conventional ADC and diffusion kurtosis model (DKI) parameters to IDF fit fractions. Non-linear fit was performed for different b-value subsets, including clinical SOC prostate DWI subset.

FIG. 4B illustrates the IDF model applied to a prostate cancer (PCa) sample. The IDF model was used to analyze lesion density for 6 PCa subjects with Gleason score (GS) 6 and 7 lesions present in the same prostate labeled by deep annotation from whole mount histopathology registered to T2-weighted images. The example in vivo multi-b DWI data set for the PCa was shared through The Cancer Imaging Archive (TCIA) as de-identified DICOM. The PCa DWI were acquired using endo-rectal (E-R) coil and 4 mm thick axial slices for 10 b-values (b=0, 0.01, 0.025, 0.05, 0.08, 0.1, 0.2, 0.5, 1.2 ms/$\mu m^2$) with TE=68 or 99 ms; TR=4 s; pixel size 1.5×1.5 or 2×2 mm$^2$. Selected 6 subjects had lesions that spanned 3 slices and had linear size>1 cm. Similar to the phantom, conventional ADC and DKI parameters were compared to IDF model fit fractions using 4-b subset (b=0, 0.2, 1, 2 ms/$\mu m^2$) and body-temperature free water diffusion rate $D_f$=3 $\mu m^2$/ms. Analysis region of interest (ROI) was manually defined on a middle lesion slice with one acquired voxel (2 mm) away from boundary in each dimension to minimize partial volume effects.

As shown in FIG. 4B, the IDF model performance was compared to conventional ADC and isotropic kurtosis model parameters: apparent diffusion, $D_a$, and kurtosis, $K_a$. The nonlinear IDF model fit 300 (Eq.1) was performed for b>=0.1 ms/$\mu m^2$ of kurtosis phantom and PCa. All fit fractions were constrained between 0 and 1 (0 & 0.9 for in vivo $F_{fc}$). For the phantom, non-linear IDF was compared for 8 b-values $0.1<b<2$ ms/$\mu$m$^2$ versus clinical PCa SOC 4-b subsets (b=0, 0.1, 0.8, 1.5 ms/$\mu$m$^2$) and (b=0, 0.2, 1, 2 ms/$\mu$m$^2$), and versus DLS size measurements. Linear (3-b) (Eq. 3) versus non-linear (4-b) (Eq. 1) IDF was performed to estimate linear fit bias. Unconstrained linear fits were performed for ME ADC: $\log(F_{ADC})$–ADC·b; kurtosis: $-D_a b+K_a(D_a b)^2/6$), and the linear IDF$_L$ models (Eq. 3). The Linear IDF$_L$ model fit utilized a subset of b>0 values typical for clinical DWI protocols (ms/$\mu$m$^2$): 1 and 2 (PCa), and (0.8, 1.5) and (1, 2) (phantom). Conventional ME ADC fit used b-values $0.1<b<1$ ms/$\mu$m$^2$, corresponding to PIRADS v2.1, while kurtosis fit was performed for 4-b SOC subset. The same ROIs were applied to all quantitative parametric maps for performance evaluation for mean diffusion parameters.

The IDF model exhibited good fit fidelity for multi- and mono-exponential DWI signal decay with b-value observed both in phantom and in vivo (FIGS. 4A and 4B, dashed curves, Table 1). The fit fractions for phantom reflected water content in free (e.g., V2) and uncoordinated compartment (e.g., V3). Among Table 1 fit-fractions for a single voxel, IDF provided the highest contrast between GS6 and GS7 cancers (11%), as well as, GS7 cancer versus nTZ (40%). Non-linear IDF was nominally independent of the selected subset (8 or 4 b-values), showing that the model fit would be robust for SOC clinical PCa protocol variations.

TABLE 1

IDF model nonlinear fit fractions (±2%) for single-voxel DWI of phantom V1-V3 vials, and PCa normal transition zone (nTZ) and Gleason GS6, GS7 lesions in FIG. 4B.

| (%)\Sample | V1 | V2 | V3 | GS7 | GS6 | nTZ |
|---|---|---|---|---|---|---|
| $F_p$ | .01 | .01 | .02 | 4.0 | 8.5 | 12.1 |
| $F_f$ | 15.1 | 51.2 | 1.4 | 19.9 | 20.3 | 40.6 |
| $F_{fc}$ | 16.7 | 6.1 | 59.4 | 12.5 | 18.4 | 25.1 |
| IDF | 68.2 | 42.7 | 39.2 | 63.6 | 52.8 | 22.3 |

Figure 5:
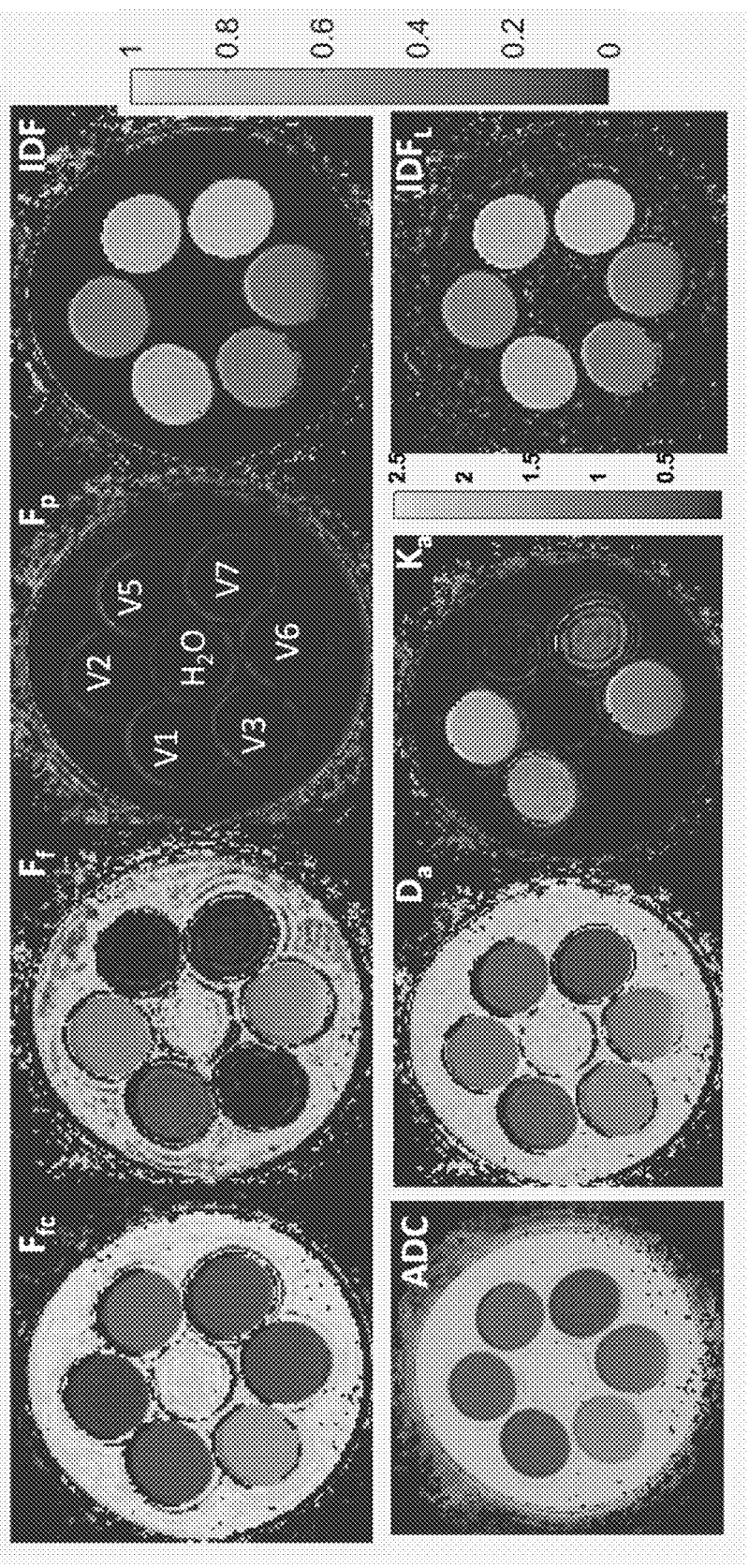
FIG. 5 illustrates parametric maps under different conditions for phantom samples. The top row of FIG. 5 illustrates parametric maps fit fractions of an example IDF nonlinear model applied to a quantitative kurtosis phantom sample, specifically showing parametric maps for $F_{fc}$, $F_f$, $F_p$, and IDF. The bottom row shows parametric maps derived from linear fits for PIRADS ADC($b_{max}$=1 ms/μm²), $D_a$ (mm²/ms), $K_a$, and a linear $IDF_L$ model. The phantom sample-vial labels are marked on the $F_p$ parametric map. Common scale for all fraction-maps is shown on the right color-bar, while metric-specific color-bars accompany ADC, $D_a$, and $K_a$ parametric maps are shown. Except for ADC and $D_a$ (units of μm²/ms), all map scales are dimensionless.

FIG. 5 illustrates a comparison of parametric maps for different diffusion models for a quantitative DWI phantom, showing the differences between a nonlinear IDF, linear IDF, and conventional DWI imaging techniques. The parametric maps illustrate the relationships among fit contrasts and undelaying physical properties. The composition of the DWI phantom is shown, formed of V1, V2, V3, V5, V6, V&, and bulk free water (H$_2$O). For the mono-exponential (single nano-scale compartment) PVP diffusion medium in V3 and V5, relative ADC and D$_a$ images exhibited scaling similar to that of F$_{fc}$ (inverse of the PVP concentration), with appropriately observed zero kurtosis, K$_a$, and no bulk free water fraction, F$_f$. For the two-compartment vesicular V1 & V2, relative F$_f$ apparently scaled similar to D$_a$ and Ka contrasts, but inverse of the IDF map. Fit perfusion fraction was appropriately absent, and F$_{fc}$+F$_f$ contribution was effectively eliminated in the IDF map with finite SNR-induced degeneracy near fit $F_k+F_f\tilde{\ }1$ (middle vial and bulk surrounding water). Thus, as shown, the IDF map summarized increasing water coordination both for single and two-compartment phantoms on a positive linear scale. The Linear IDF$_L$ fit exhibited finite positive bias compared to the non-linear IDF model fit, increasing for higher F$_{fc}$+F$_f$>0.5. For instance, in V2 multi-compartment materials with smaller vesicles and higher F$_f$ (FIG. 4A, Table 1), the apparent linear IDF$_L$ values are higher than nonlinear IDF (FIG. 3).

Figures 6A, 6B, 6C:
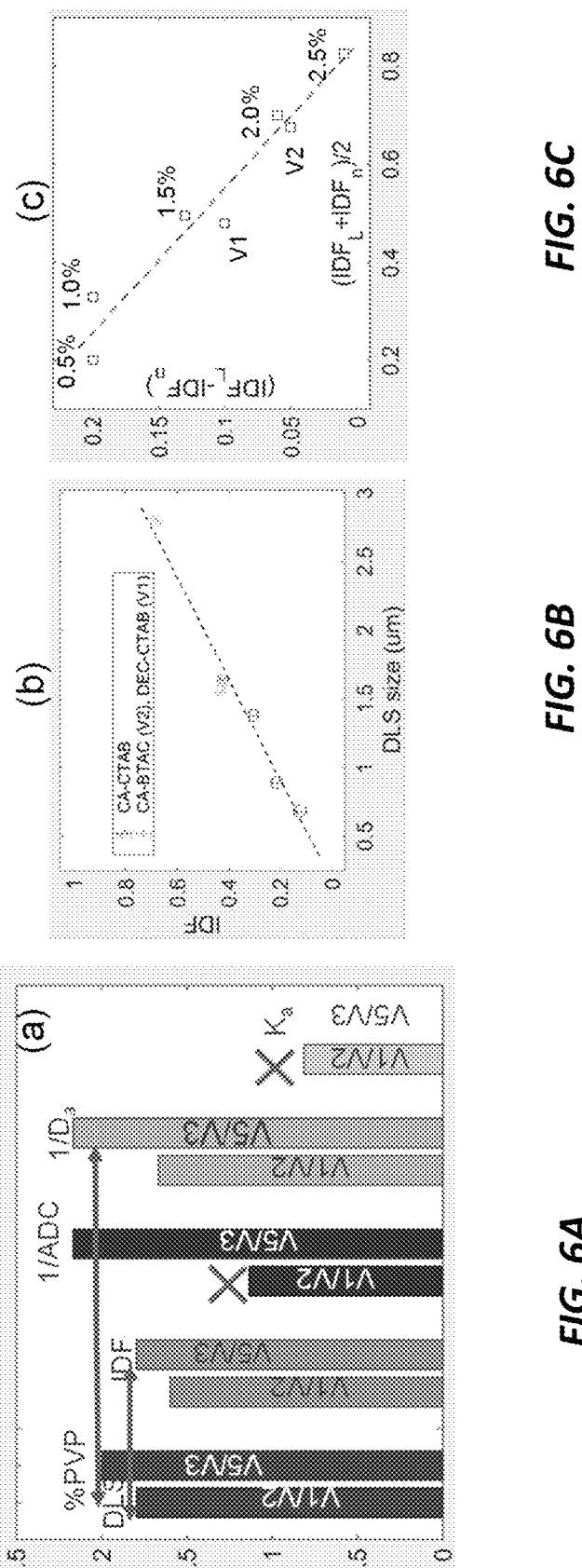
FIG. 6A is a bar-plot of relative phantom characteristics for V1/V2 and V5/V3 phantom samples, showing a comparison for DLS-derived vesicle sizes and PVP concentrations (dark green) versus different diffusion model parameters: IDF (light green), inverse ADC (dark blue), inverse apparent diffusion (cyan) and apparent kurtosis (gray, no $K_a$ values for mono-exponential V5/V3, $K_a{\sim}0$). Horizontal arrows connect the diffusion parameters with the highest correlation to physical phantom properties. Magenta crosses mark the trends opposite to physical property ratios.
FIG. 6B is a plot illustrating an observed linear relation between IDF and DLS vesicle size for V1: DEC-CTAB, V2: CA-BTAC (cyan) and CA-CTAB (3:1 to 6:1, blue) samples.
FIG. 6C shows an example linear $IDF_L$ model bias with respect to non-linear fit IDF measured for CA-CTAB (3:1) phantoms at different concentrations (0.5% to 2.5%, marked on the graph), as well as, for V1 and V2 phantoms. The dashed lines

FIG. 6A-6C Illustrate the performance of an example IDF model in accordance with the present techniques versus physical phantom properties. FIG. 6A is a bar-plot of relative characteristics for V1/V2 and V5/V3 phantom samples, comparing values for DLS-derived vesicle sizes and PVP concentrations (dark green) versus different diffusion model parameters: IDF (light green), inverse ADC (dark blue), inverse apparent diffusion, D$_a$, (cyan) and apparent kurtosis (gray, no K$_a$ values for mono-exponential V5/V3, K$_a\tilde{\ }0$). Horizontal arrows connect the diffusion parameters with the highest correlation to physical phantom properties. Crosses mark the trends opposite to physical property ratios. FIG. 6A shows that relative IDF and inverse D$_a$ contrasts apparently linearly scaled with vesicle size (volume to surface ratio, V/S V2:V1$\tilde{\ }$1.8) and PVP concentration (V3:V5$\tilde{\ }$2), while apparent kurtosis and inverse ADC did not properly reflect micro-restriction within vesicles. Relative D$_a$ contrast (V2:V1$\tilde{\ }$1.7) was closer to V/S of phantom compartments than K$_a$ (V2:V1$\tilde{\ }$1.2). The IDF ratios (V1:V2$\tilde{\ }$1.6; V5:V3$\tilde{\ }$1.8) provided closest reflection of phantom physical properties both for mono-exponential (% PVP) and multi-exponential diffusion media (V/S), consistent with water coordination metric assumed by the IDF model 300 in FIG. 1.

FIG. 6B Illustrates an observed linear relation between IDF and DLS vesicle size for V1: DEC-CTAB, V2: CA-BTAC (cyan) and CA-CTAB (3:1 to 6:1, blue) samples. FIG. 6C shows a linear IDF$_L$ bias with respect to non-linear fit IDF measured for CA-CTAB (3:1) phantoms at different concentrations (0.5% to 2.5%, marked on the graph), as well as, and V1 and V2 phantoms. The dashed lines in FIGS. 6B and 6C highlight linear dependence for phantom IDF versus size titration and IDF$_L$ bias trends, respectively.

That is, IDF model calibration (FIG. 4B) shows a linear relation between IDF and V/S for micro-vesicles between 0.5 to 3 $\mu$m apparently, independent of chemical constituents that can be applied for vesicular phantom titration of quantitative diffusion parameters. Thus, the calibrated diffusion phantom can be used for testing acquisition and fit protocol bias in MRI equipment and/or in DWI measurements in general. Linear IDF$_L$ fit bias versus non-linear IDF was increasing for phantom IDF<0.8 from 5% up to 20% with apparent dependence on sample F$_{fc}$/F$_f$. This bias would depend on the low b-value used for the linear fit (deviation from assumption of negligible free water contribution, Eq. 3, FIG. 3) and could generally lead to IDF$_L$ overestimate for low-density tissue. The performed phantom analysis (FIG. 4A) illustrates example workflow that could be used for linear IDF$_L$ bias assessment and correction to restore higher contrast between low and high-density lesions for abbreviated acquisition protocols enabled by linear IDF$_L$.

Figure 7:
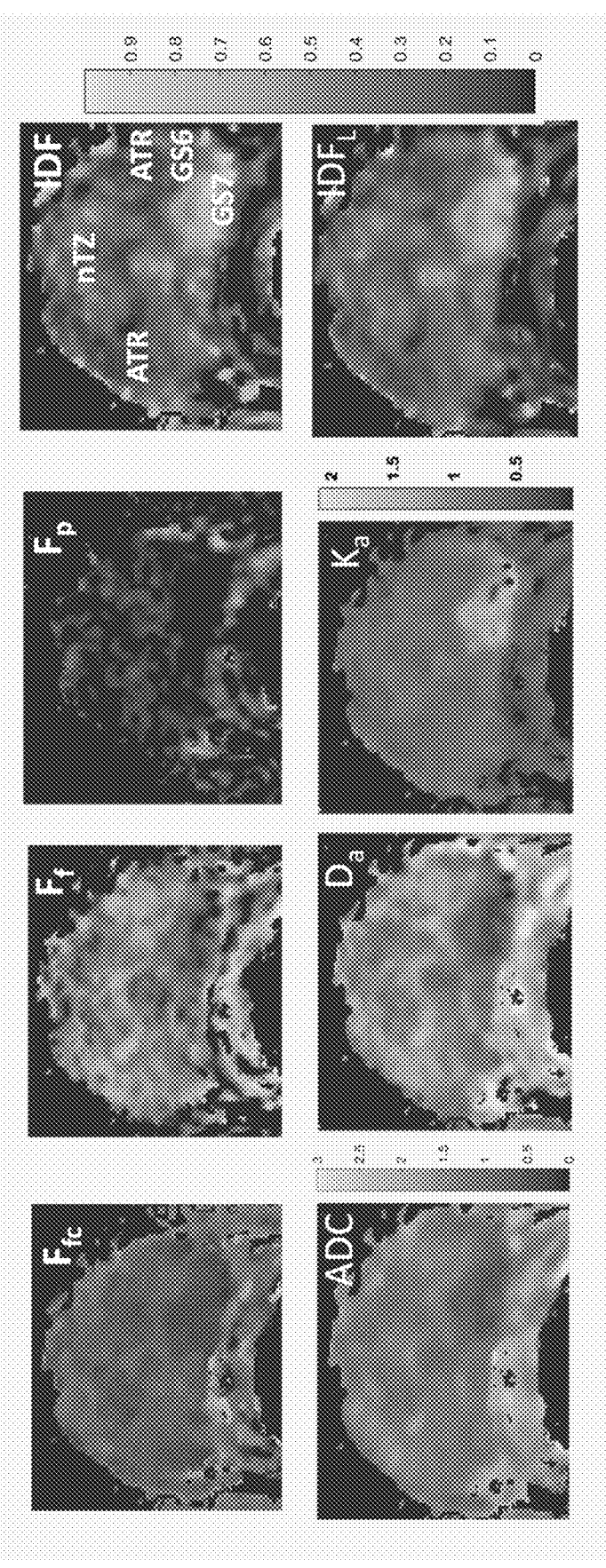
FIG. 7 parametric maps from different diffusion models for a prostate cancer sample (PCa). The top row illustrates the IDF model nonlinear fit fractions of the PCa sample, specifically showing parametric maps for $F_{fc}$, $F_f$ $F_p$, and IDF. The bottom row shows parametric maps derived from linear fits for PIRADS SOC ADC($b_{max}$=1 ms/μm²), $D_a$, $K_a$, and a linear $IDF_L$ model. A common scale for all fraction-maps is shown on the right color-bar, while metric-specific color-bars accompany ADC, $D_a$, and $K_a$ parametric maps. Except ADC and $D_a$ (units of μm²/ms), all map scales are dimensionless. The PCa parametric maps are shown for a single slice image with right-left atrophy (ATR) and mixed GS7 (geographic) neighboring GS6 (linear) tumor in base right peripheral zone (PZ), and normal transition zone (nTZ, middle), corresponding to histopathology labeling.

FIG. 7 illustrates parametric maps for an IDF model of the prostate, in particular showing nonlinear fit fractions of an example subject with prostate cancer (PCa). Shown in the top row from left-to-right are parametric maps of F$_{fc}$, F$_f$, F$_p$, and IDF. The bottom row shows parametric maps derived from linear fits for PIRADS ADC($b_{max}$=1 ms/$\mu$m$^2$), D$_a$, K$_a$, and linear IDF$_L$. A common scale for all fraction-maps is shown on the right color-bar, while metric-specific color-bars accompany ADC, D$_a$, and K$_a$ parametric maps. Except for the ADC and D$_a$ (units of $\mu$m$^2$/ms) maps, all map scales are unitless. PCa parametric maps are shown for a single slice image with right-left atrophy (ATR) and mixed GS7 (geographic) neighboring GS6 (linear) tumor in base right peripheral zone (PZ), and normal transition zone (nTZ, middle), corresponding to histopathology labeling from Hurrel, et al. (Hurrel S L, McGarry S D, Amy Kaczma-rowski A, Iczkowsk K A, et al. Optimized b-value selection for the discrimination of prostate cancer grades, including the cribriform pattern, using diffusion weighted imaging. J Med. Imaging 2017, 5:011004).

As shown in FIG. 7, the IDF model for the prostate effectively eliminated free (luminal) water contribution from large (sub-mm) secretory ducts and blood vessels confounding $D_a$ map in transition zone (nTZ) and in the prostate base. The IDF model also enhanced contrast between left-right atrophy (low IDF) in the peripheral zone (PZ) and nTZ tissue (middle) compared to $D_a$, $K_a$ or ADC. For the GS6/ GS7 lesion, IDF model evidently captured complementary $K_a$~$1/D_a$ contrast information, visually most similar to $1/ADC$, but on a linear (fraction) scale. Prostate IDF scaled positively & linearly with the lesion density (increasing from atrophy to GS6 and GS7). Similar to phantom results, the linear $IDF_L$ model showed positive bias for lower IDF values (e.g., in atrophy regions) decreasing its contrast versus higher density tumor compared to the nonlinear IDF model. PCa fit IDF values were increasing with increasing malignancy, consistent with increasing tissue density and macromolecule crowding. It is noteworthy that IDF measurement would be sensitive to lesion segmentation (particularly challenging for linear lesions, FIG. 7), because some cancer lesions were neighboring atrophy, which could confound the measured IDF values (and other parameters) by partial volume effects.

Figure 8B:
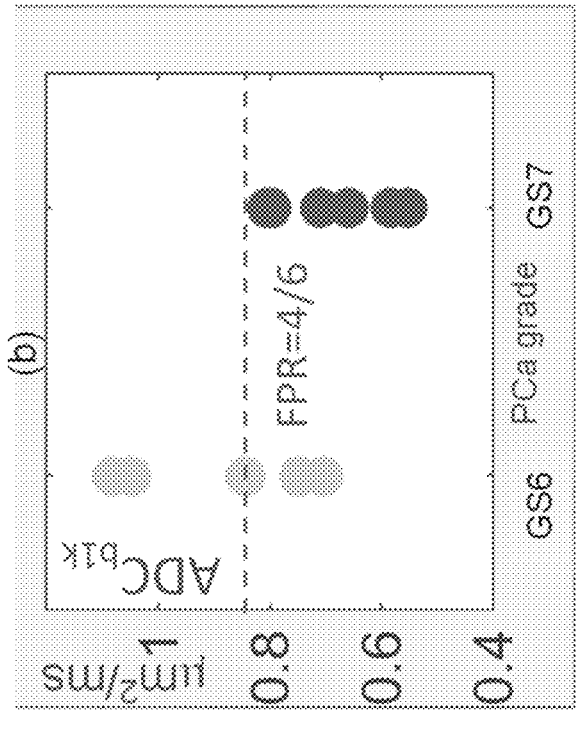
FIGS. 8A and 8B illustrate scatter plots of region of interest (ROI)-mean IDF and PIRADS ADC versus Gleason score (GS) for 12 PCa lesions exhibiting improved false positive rate (FPR) for IDF>0.55 compared to ADC<0.85 mm²/ms.
Figure 8A:
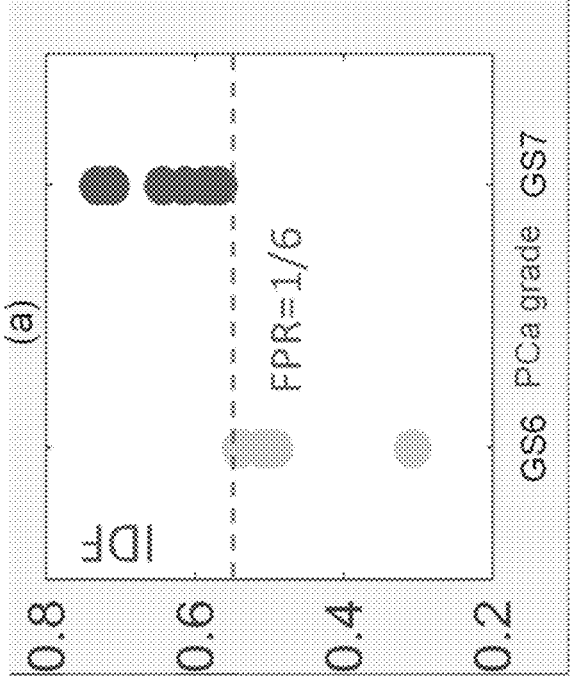

FIGS. 8A and 8B are scatter plots showing a region of interest mean IDF value (FIG. 8A) and PIRAD ADC values (FIG. 8B) versus Gleason score (GS) for 12 PCa lesions. The scatter plots exhibit improved false positive rate (FPR) for the IDF models herein versus PIRAD ADC, where the threshold with zero false negative for GS7 is determined to be IDF>0.55 and the threshold for PIRAD ADC is determined to be ADC<0.85 mm²/ms (thresholds marked by dashed horizontal lines at the highest specificity for aggressive GS7 detection). The analysis results for the 12 PCa lesions indicate that the IDF model reduces false positive rates for the GS6 versus GS7 lesion differentiation to FPR=1/6 compared to standard PIRADS ADC (FPR=4/6).

Thus, these scatter plots demonstrate an example process for determining IDF thresholds and ranges to be applied to like samples. For example, the preliminary results summarized in FIG. 8A suggest that for a small lesion samples, an IDF threshold of 0.55 could be used for detection of aggressive prostate cancers, and perform at least as reliably as ADC<0.85 m²/ms in determine true positives, but with lower FPR. To determine an IDF threshold for cancer identification, as compared to the 12 lesions study shown with good SNR provided by E-R coil, a larger study sampling wider ranges of lesion densities with different coil could be performed and an IDF threshold determined from the sample.

In some examples, the absolute thresholds may also depend on acquisition TR and TE due to compartmental T1 and T2 bias, which could be accounted for by analytical modeling, e.g., as shown with the model of Eq.2. Therefore, in some examples, the IDF model is implemented to create a diagnostic assay workflow that incorporates bias correction both for the fit and acquisition protocol to determine a threshold on a training group of subjects, and apply that to a test group for validation. Because both IDF model and acquisition protocols do not include organ-dependent assumptions, the proposed assay strategy can be generalized to multiple organ cancers.

The techniques herein and resulting IDF models can provide several benefits. The IDF model can eliminate capillary and bulk luminal water background by incorporating built-in model constraints for compartment diffusion rates based on reported values from independent studies or based on developed fit constraints (such as fit fractions, intercept, slope, etc. described herein). Additionally, the IDF model linearly scales with volume-to-surface ratio (e.g., tissue density) of micro-compartment and macromolecular concentration. The IDF model can be organ tissue independent. For example, the IDF model suggested organ independent b-range between 1 and 2 ms/µm² effective for tumor grading. That range allows the IDF model to be applicable for current clinical standard of care DWI protocols, thereby allowing analysis of previously captured DWI image data, as well as allowing the large databases of existing DWI images to be used for model training and development.

IDF model has several limitations: it does not inform on compartment localization (extra-versus intra-cellular); exhibits finite degeneracy due to SNR bias when combined free and uncoordinated fractions are close to 1 for low-density (e.g., atrophy or necrotic) tissue. The latter could be improved by including noise model, but would require more b-values acquired. More practical solution would be to calibrate the bias for non-linear versus linear fit using phantom, as was shown in this work, and apply retrospective bias correction. Furthermore, fit fractions are T2- and T1-weighted, hence would dependent on TE and TR (require DWI protocol standardization). This protocol-dependent bias may also be accounted for retrospectively by simulation. Additionally, in general the rate of collective diffusion, D, for coordinated water depends on distribution of macromole sizes. Finally, for all quantitative metrics the acquired DWI resolution would limit analyzable tumor lesion size free of partial volume effect. Cancer lesions of different grades and density can be in close proximity, confounding accuracy of measured fractions. To reliably avoid partial volume effects, it is best to make measurements one voxel away from the lesion boundary. With acquired voxel of 2 mm, the minimum detectible "linear" lesion size is 6 mm. In reality, due to through-slice resolution of 4 mm, measureable through-slice lesion size is 12 mm. Through-slice resolution would limit accurate grade assignment for small PCa lesions.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A computer-implemented method of analyzing diffusion weighted images, the computer-implemented method comprising:

receiving, at one or more processors, diffusion weighted image (DWI) data corresponding to a sample of an imaged tissue and identifying within the DWI data a region of interest comprising one or more voxels, the region of interest spanning at least partially a tissue region within the sample;

applying, using the one or more processors, the DWI data corresponding to the region of interest to an impeded diffusion fraction model and, from applying the impeded diffusion fraction model, determining an impeded diffusion fraction for each of the one or more voxels in the region of interest, the impeded diffusion fraction model being a multi-compartment model of water coordination by macromolecules agnostic to tissue compartment origin and applicable across multiple tissue compartments using a fixed rate for free diffusion and order of magnitude scaling constraints for vascular diffusion and coordinated diffusion;

from the impeded diffusion fraction of the one or more voxels, identifying the presence and/or severity of a pathology in the imaged tissue; and generating, using the one or more processors and the identified presence and/or severity of the pathology in the imaged tissue, a pathology determination image indicating a location of the presence and/or the severity of the pathology within the region of interest.

2. The computer-implemented method of claim 1, wherein the multiple tissue compartments comprise a cellular compartment, a free water compartment, and a vascular compartment.

3. The computer-implemented method of claim 1, wherein the impeded diffusion fraction model comprises an expression for nonlinear impeded diffusion fraction (IDF):

$$\frac{S_b}{S_0} \approx F_f E_f + (1 - F_p - F_f)E_c; E_f = \exp(-bD_f); E_c \approx \exp(-bF_{fc}D_f);$$

$$IDF = 1 - F_p - F_f - F_{fc}$$

where Sb is the DWI signal intensity as a function of b-value, S0 is signal intensity at b=0, b are three or more b-values between 0.1 and 2 ms/μm2 (one or more>1 ms/μm2) Df is free diffusion rate, Fp is a pseudo diffusion fraction corresponding to a vascular compartment, Ff is a free water fraction, and Ffc is an uncoordinated water fraction in a cellular compartment.

4. The computer-implemented method of claim 1, wherein the impeded diffusion fraction model comprises an expression for a linear impeded diffusion fraction (IDFL):

$$\log\left(\frac{S_b}{S_0}\right) = C_1 + C_2 \cdot b; F_{fc} = -C_2/D_f;$$

$$F_c = \exp(C_1); IDF_L = \exp(C_1) + C_2/D_f$$

where Sb is the DWI signal intensity as a function of b-value, S0 is signal intensity at b=0, C1 is the linear fit intercept, C2 is a linear fit slope, b are two or more b-values between 0.6 and 2 ms/μm2 (one or more>1 ms/μm2) linear fit intercept, Df is free diffusion rate, and Fc is cellular fraction, for each of the one of more voxels.

5. The computer-implemented method of claim 1, wherein the impeded diffusion fraction model comprises an nonlinear fit impeded diffusion fraction.

6. The computer-implemented method of claim 5, wherein the nonlinear fit impeded diffusion fraction comprises fit constraints.

7. The computer-implemented method of claim 1, wherein the impeded diffusion fraction model comprises a linear fit impeded diffusion fraction.

8. The computer-implemented method of claim 7, wherein the linear fit impeded diffusion fraction comprises fit constraints.

9. The computer-implemented method of claim 1, wherein the DWI data comprises image data of the sample and comprising a plurality of voxels, the method further comprising:

prior to applying the DWI data to the impeded diffusion fraction model, identifying from the plurality of voxels, voxels satisfying a threshold voxel signal threshold condition and applying, as the DWI data, those voxels satisfying the threshold voxel signal threshold condition.

10. The computer-implemented method of claim 1, wherein the DWI data comprises image data of the sample and comprising a plurality of voxels, the method further comprising:

prior to applying the DWI data to the impeded diffusion fraction model, identifying from the plurality of voxels, voxels corresponding to a boundary region between normal tissue and lesion indicating tissue, and excluding, from the DWI data, those voxels corresponding to the boundary region.

11. The computer-implemented method of claim 1, wherein the DWI data comprises a plurality of voxels and wherein identifying the presence of a pathology in the imaged tissue comprises:

determining the impeded diffusion fraction for each of a plurality of voxels, determining a statistical summary metric of impeded diffusion fraction from the plurality of impeded diffusion fractions, and identifying the presence of the pathology from the summary metric for impeded diffusion fraction.

12. The computer-implemented method of claim 11, wherein the statistical summary metric for the plurality of voxels within region of interest is any mathematical histograms characteristic (moment), or percentiles.

13. The computer-implemented method of claim 11, wherein identifying the presence of a pathology in the imaged tissue comprises: determining if the impeded diffusion fraction is above a threshold value of the statistical summary metric, the threshold value corresponding to the presence of the pathogen.

14. The computer-implemented method of claim 1, wherein identifying the presence of a pathology in the imaged tissue-comprises: determining if the impeded diffusion fraction is above a threshold value, the threshold value corresponding to the presence of the pathogen.

15. The computer-implemented method of claim 14, wherein the threshold value is determined from retrospective DWI analysis and adjusted for acquisition protocol bias in T1 and T2 weighting and b-range.

16. The computer-implemented method of claim 1, wherein the pathogen is cancer.

17. The computer-implemented method of claim 1, wherein the pathogen is cancer severity.

18. The computer-implemented method of claim 1, wherein the pathology is cancer and the sample is taken from disease tissue, the method further comprising, after performing a treatment on the subject:

receiving, at one or more processors, subsequent DWI data corresponding to a subsequent sample taken from the disease tissue, and identifying within the subsequent DWI data one or more voxels corresponding to the region of interest;

applying, using the one or more processors, the subsequent DWI data to the impeded diffusion fraction model and determining the presence of a change in the impeded diffusion fraction from the impeded diffusion fraction determined from the DWI data; and from the presence of the change in the impeded diffusion fraction, determining an efficacy of the treatment on the subject.

19. The computer-implemented method of claim 16, wherein the cancer is prostate cancer, breast cancer, or pancreatic cancer.

* * * * *